(12) United States Patent
Sheehy

(10) Patent No.: US 10,322,268 B2
(45) Date of Patent: Jun. 18, 2019

(54) SYSTEMS AND METHODS FOR A CEREBROSPINAL FLUID FLOW DETECTOR

(71) Applicant: DIGNITY HEALTH, San Francisco, CA (US)

(72) Inventor: John Paul Sheehy, San Francisco, CA (US)

(73) Assignee: DIGNITY HEALTH, San Francisco, CA (US)

( * ) Notice: Subject to any disclaimer, the term of this patent is extended or adjusted under 35 U.S.C. 154(b) by 0 days.

(21) Appl. No.: 15/770,579

(22) PCT Filed: Apr. 20, 2017

(86) PCT No.: PCT/US2017/028536
§ 371 (c)(1),
(2) Date: Apr. 24, 2018

(87) PCT Pub. No.: WO2017/184824
PCT Pub. Date: Oct. 26, 2017

(65) Prior Publication Data
US 2018/0311485 A1    Nov. 1, 2018

Related U.S. Application Data

(60) Provisional application No. 62/324,971, filed on Apr. 20, 2016.

(51) Int. Cl.
*A61B 5/00* (2006.01)
*A61B 90/00* (2016.01)
(Continued)

(52) U.S. Cl.
CPC .......... *A61M 27/006* (2013.01); *A61B 5/00* (2013.01); *A61B 5/032* (2013.01); *A61B 5/4064* (2013.01);
(Continued)

(58) Field of Classification Search
CPC ......... A61B 5/032; A61B 5/4064; A61B 5/00; A61B 5/6852; A61B 5/6868; A61B 6/486; A61B 90/39; A61M 27/00; A61M 27/006
See application file for complete search history.

(56) References Cited

U.S. PATENT DOCUMENTS

| 2007/0204787 A1 | 9/2007 | Donehue |
| 2009/0024072 A1* | 1/2009 | Criado .................. A61M 25/10 604/9 |

(Continued)

*Primary Examiner* — Leslie R Deak
(74) *Attorney, Agent, or Firm* — Polsinelli PC

(57) ABSTRACT

Embodiments for a cerebrospinal fluid flow detector for detecting the flow of cerebrospinal fluid are disclosed. In some embodiments, the cerebrospinal fluid flow detector includes a casing with a rotatable wheel having a plurality of radially extending arms disposed therein. The rotatable wheel is in communication with a channel having a distal end in communication with an inlet port and a proximal end in communication with an outlet port such that the flow of cerebrospinal fluid through the channel causes the rotatable wheel to rotate. In some embodiments, each radially extending arm includes at least one radiopaque marker in which movement of the rotatable wheel caused by fluid flow through the channel allows an X-ray imaging apparatus to detect the difference in position of a respective radiopaque marker at multiple times caused by rotation of the rotatable wheel.

18 Claims, 6 Drawing Sheets

(51) Int. Cl.
  *A61M 27/00* (2006.01)
  *A61B 5/03* (2006.01)
  *A61B 6/00* (2006.01)

(52) U.S. Cl.
  CPC ........... *A61M 27/00* (2013.01); *A61B 5/6852* (2013.01); *A61B 5/6868* (2013.01); *A61B 6/486* (2013.01); *A61B 90/39* (2016.02)

(56) References Cited

U.S. PATENT DOCUMENTS

2012/0240689 A1  9/2012  Smith
2014/0207043 A1  7/2014  Anand et al.
2016/0220794 A1* 8/2016  Negre ................. A61M 27/006

* cited by examiner

SYSTEMS AND METHODS FOR A CEREBROSPINAL FLUID FLOW DETECTOR

FIELD

The present disclosure generally relates to a fluid flow detector, and in particular to systems and methods for a fluid flow detector having a rotary wheel that allows detection of cerebrospinal fluid based on movement of the rotary wheel in the presence of cerebrospinal fluid flow through the fluid flow detector.

BACKGROUND

Shunts are medical devices having various tubes referred to as catheters. Shunts are minimally used to allow excess fluids that build up in one portion of the body to be drained into another portion of the body, thereby normalizing fluid flow pressure in the first portion of the body. Typically, patients are implanted with one or more catheters, separated by one or more one-way valves to allow the excess fluid to periodically drain from the over-pressurized area in the body.

In particular, ventriculoperitoneal shunts are used to treat patient with hydrocephalus. These shunts allow passage of cerebrospinal fluid from the ventricles in the brain to the peritoneal cavity. Due to the excess protein levels in the cerebrospinal fluid of these patients, the shunt valves often become occluded.

In addition, there have been numerous issues associated with shunt systems intended to drain cerebrospinal fluid from the brain to the peritoneal cavity. For various reasons, such as a build-up of protein within the interior of a shunt system, kinking of a shunt catheter, or migration of the distal catheter out of the peritoneum, a shunt system may become occluded, therefore reducing or preventing the flow of cerebrospinal fluid. Symptoms of a blocked shunt system can be serious if left unchecked, and can result in frequent visitations to the emergency room.

In some cases, the ventricles in the brain in which the cerebrospinal fluid accumulates do not change size in response to elevated or depressed levels of cerebrospinal fluid. Therefore, traditional imaging techniques, such as computed tomography scanning of the brain, are unable to determine whether or not the cerebrospinal fluid flow through a shunt is occurring as intended. As a result, physicians often must resort to invasive techniques, such as a shunt tap, to detect the flow of cerebrospinal fluid. During a shunt tap, a needle is placed through the scalp into the shunt reservoir of the shunt system. The cerebrospinal fluid is then withdrawn, and the fluid pressure measured to determine if the cerebrospinal fluid has been flowing through the shunt system.

This procedure can result in a number of problems. First, the procedure can be uncomfortable for the patient and can result in an infection. Second, the procedure requires interpretation by an experienced physician, resulting in the need for the procedure to be performed at a facility with neurosurgical services.

It is with these observations in mind, among others, that various aspects of the present disclosure were conceived and developed.

BRIEF DESCRIPTION OF THE DRAWINGS

Corresponding reference characters indicate corresponding elements among the view of the drawings. The headings used in the figures do not limit the scope of the claims.

DETAILED DESCRIPTION

Figure 1:
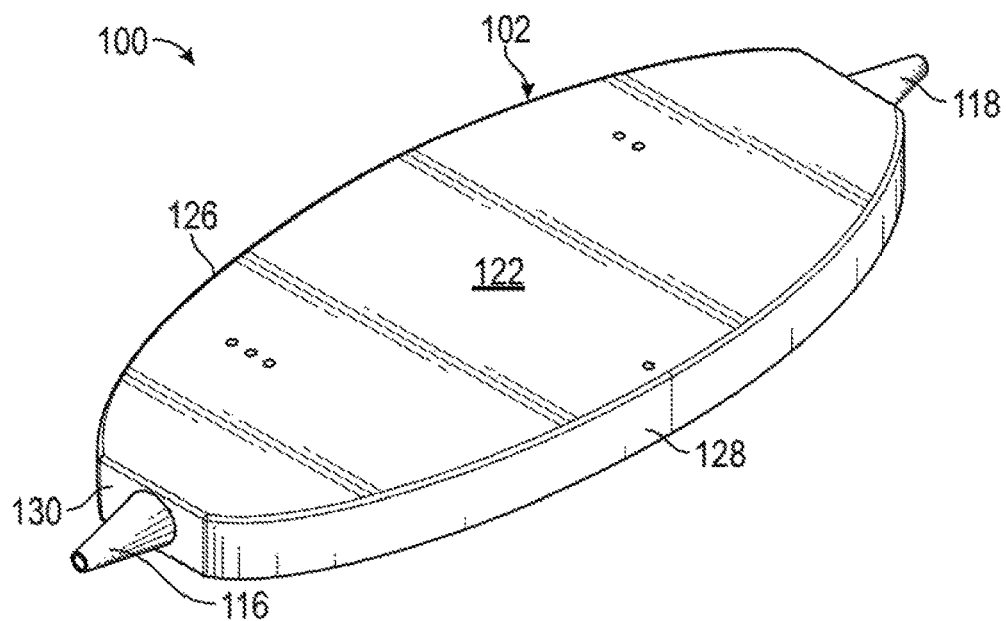
FIG. 1 is a perspective view of a fluid flow detector, according to one aspect of the present disclosure.

Various embodiments of a fluid flow detector capable of detecting the presence of cerebrospinal fluid are disclosed herein. In some embodiments, the fluid flow detector is in selective fluid flow communication with a shunt reservoir for receiving cerebrospinal fluid that passes through a shunt valve. In some embodiments, the fluid flow detector includes a casing having a wheel housing disposed therein with a rotatable wheel inside the wheel housing, the rotatable wheel housing defining a plurality of radially extending arms. The casing further includes a fluid pathway in fluid flow communication between an inlet port and an outlet port configured to permit fluid flow of cerebrospinal fluid from the shunt reservoir through the fluid flow detector. In some embodiments, at least one of the radially extending arms of the rotatable wheel is partially disposed within the fluid pathway of the channel such that any flow of cerebrospinal fluid through the channel of the fluid flow detector causes movement of the rotatable wheel due to the force of the fluid flow against one or more of the radially extending arms. In some embodiments, each radially extending arm may include at least one radiopaque marker in which movement of the rotatable wheel caused by the flow of cerebrospinal fluid through the channel allows an X-ray imaging apparatus to observe the difference in position of each respective radiopaque marker, if any, at multiple time frames. In one method of detecting the presence of cerebrospinal fluid, an X-ray imaging apparatus periodically takes a plurality of images of the radiopaque markers located on one or more of the radially extending arms such that the position of the radiopaque markers observed in each respective image may be determined to indicate whether movement of the radially extending arms has occurred, and therefore indicate the presence of cerebrospinal fluid within the fluid flow detector. Referring to the drawings, embodiments of a fluid flow detector for detecting the presence of cerebrospinal fluid are illustrated and generally indicated as 100 in FIGS. 1-13.

Figure 2:
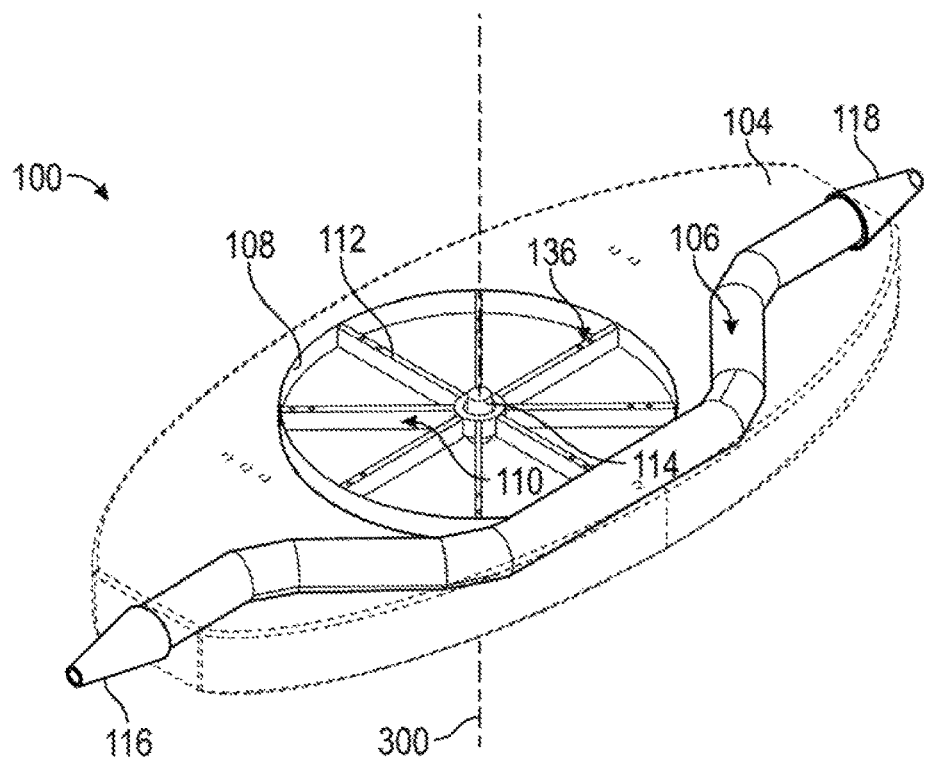
FIG. 2 is a perspective view of the fluid flow detector of FIG. 1 illustrating the body of the cerebrospinal fluid flow detector in phantom and showing the interior components thereof, according to one aspect of the present disclosure.
Figure 3:
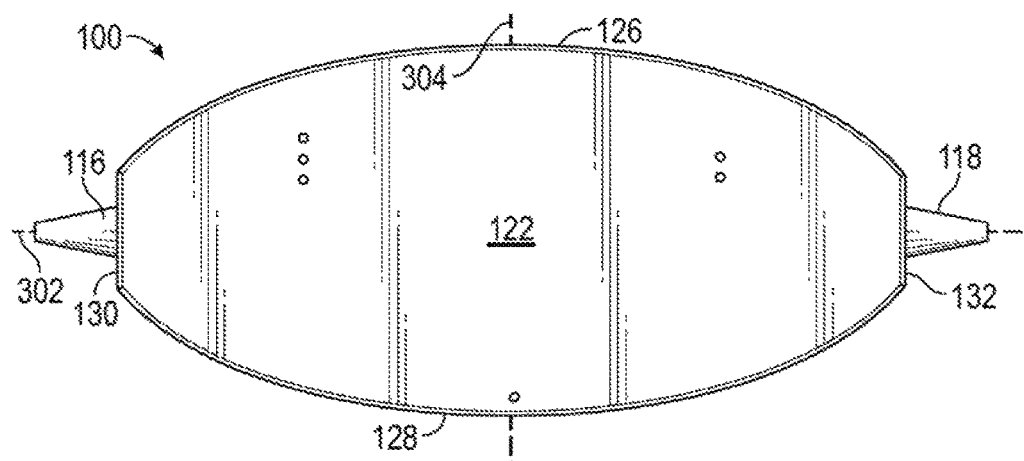
FIG. 3 is a top view of the fluid flow detector, according to one aspect of the present disclosure.
Figure 4:
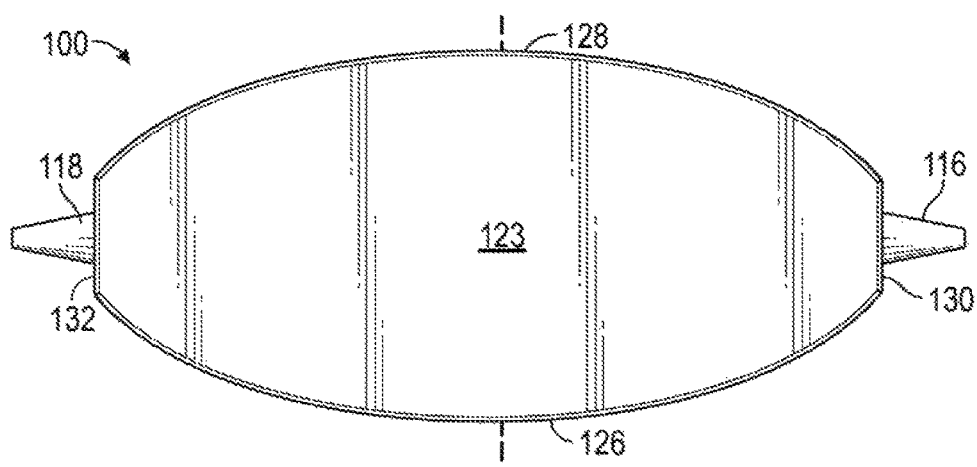
FIG. 4 is a bottom view of the fluid flow detector, according to one aspect of the present disclosure.
Figure 5:
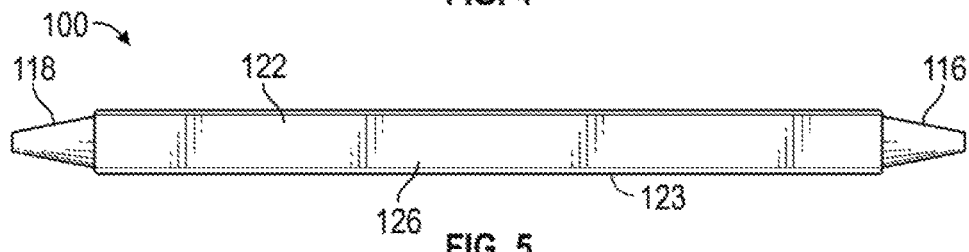
FIG. 5 is a side view of the fluid flow detector, according to one aspect of the present disclosure.
Figure 6:
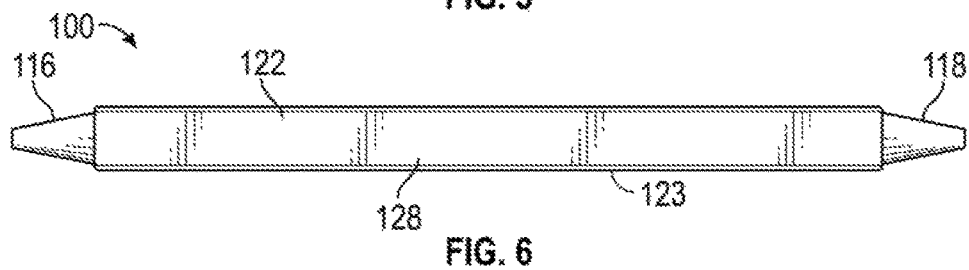
FIG. 6 is an opposite side view of the fluid flow detector, according to one aspect of the present disclosure.
Figure 7:
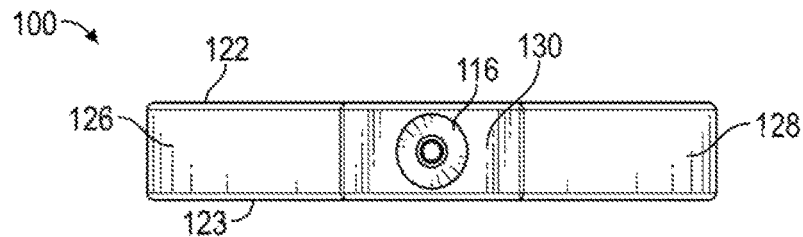
FIG. 7 is an end view of the fluid flow detector, according to one aspect of the present disclosure.
Figure 8:
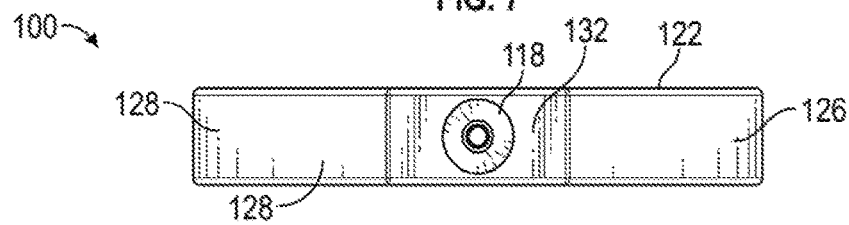
FIG. 8 is an opposite end view of the fluid flow detector, according to one aspect of the present disclosure.
Figure 11:
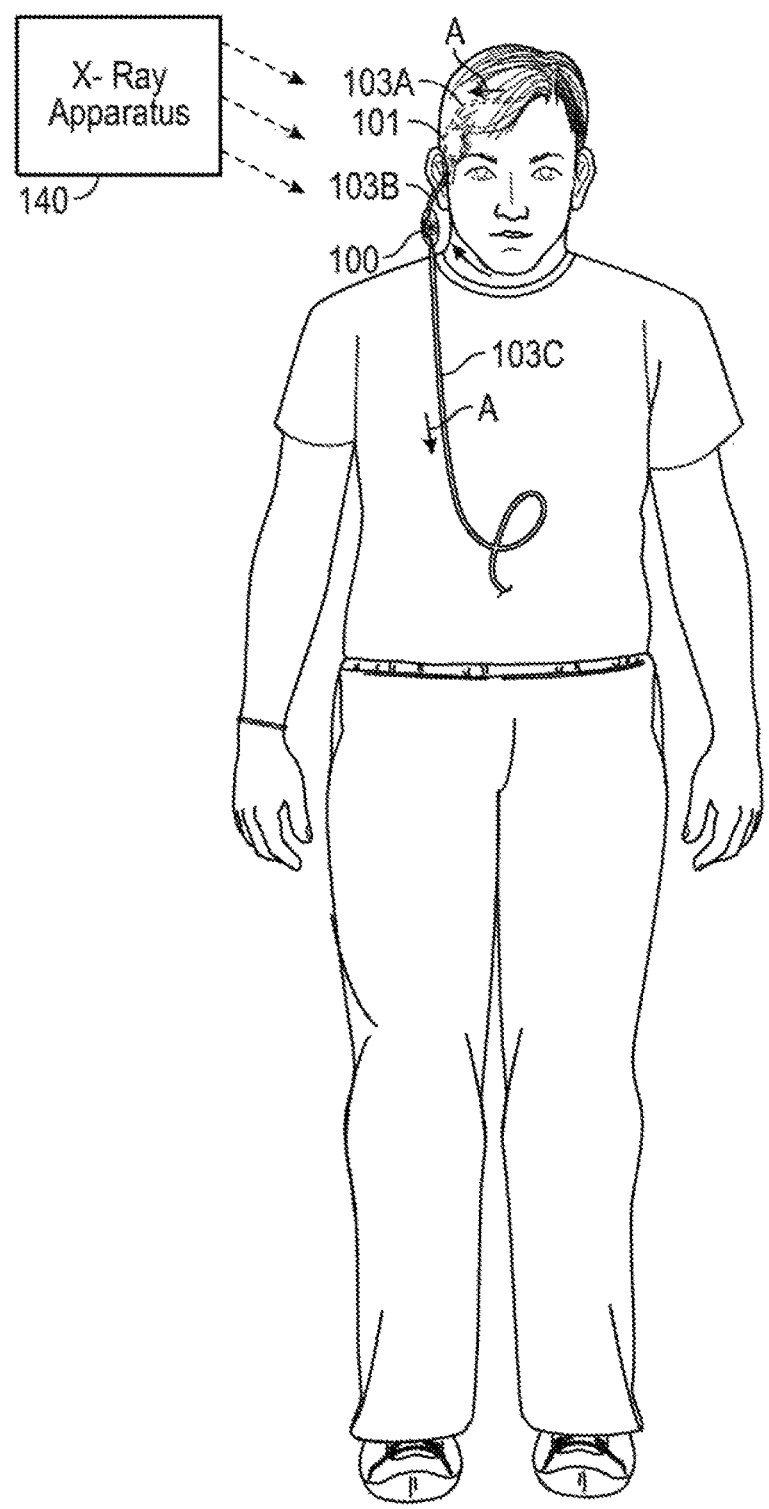
FIG. 11 is a simplified illustration showing the fluid flow detector operatively engaged between a shunt valve coupled to a ventricular catheter and a second catheter disposed within the peritoneal cavity of a subject individual, according to one aspect of the present disclosure.

Referring to FIGS. 1-8, in some embodiments the fluid flow detector 100 may include a casing 102 collectively defined by a top portion 122, a bottom portion 123, a first side portion 126, an opposite second side portion 128, a first end portion 130, and an opposite second end portion 132. In some embodiments, an inlet port 116 extends outwardly from the first end portion 130 and an outlet port 118 extends outwardly from the second end portion 132 of casing 102. In some embodiments, the inlet port 116 may include a male port configured to engage in fluid tight engagement one end of a catheter 103C (FIG. 11). As shown, the casing 102 further defines an interior chamber 104 in which a wheel housing 108 is disposed therein. In some embodiments, the wheel housing 108 defines a circular-shaped housing configured to receive a rotatable wheel 110 therein that rotates about an axis 300 as illustrated in FIG. 2.

Figure 9:
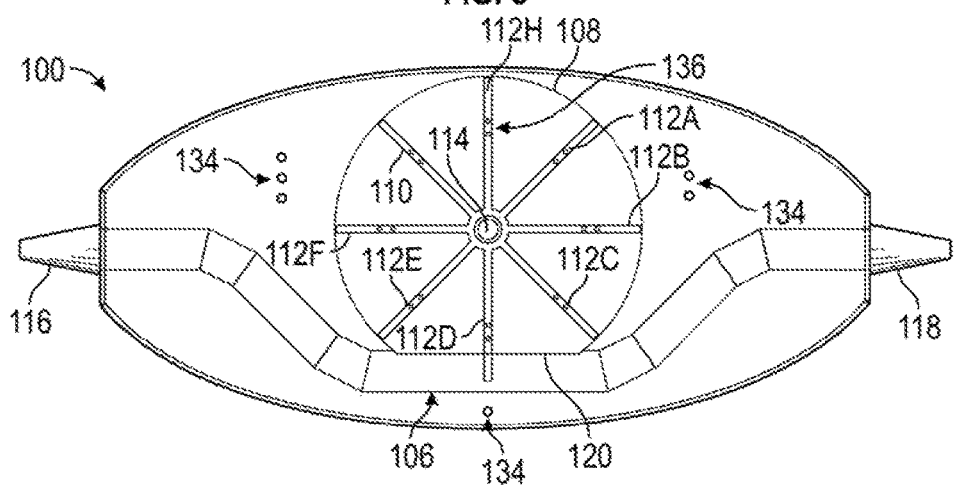
FIG. 9 is an illustration of the fluid flow detector showing a rotary wheel having a plurality of extending radial arms in communication with a channel that communicates with an inlet port and an outlet port, according to one aspect of the present disclosure.
Figure 10:
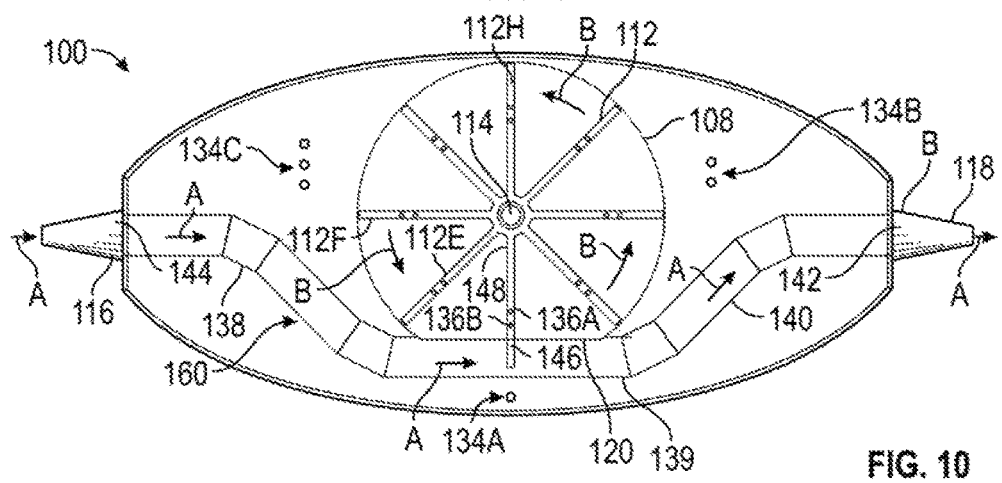
FIG. 10 is an illustration of the fluid flow detector showing the rotation of the rotary wheel and flow of fluid through the channel between the inlet and outlet ports, according to one aspect of the present disclosure.

As shown in FIGS. 2, 9 and 10, the rotatable wheel 110 defines a plurality of radially extending arms 112 in which each arm 112 extends radially from an axle 114 at the center of the rotatable wheel 110 which rotates about axis 300. In some embodiments, the rotatable wheel 110 defines eight radially extending arms 112A-112H, although in other embodiments any plurality of radially extending arms 112 sufficient to rotate the rotatable wheel 110 in the presence of cerebrospinal fluid within a channel 106 of the fluid flow detector 100 is contemplated. In some embodiments each of the radially-extending arms 112 defines an elongated member having a distal portion 146 that forms the free end of the radially extending arm 112 and a proximal portion 148 that extends radially from the axle 114, such as illustrated by radially-extending arm 112D illustrated in FIG. 9.

In some embodiments, some or all of each of the radially extending arms 112 includes at least one radiopaque marker 136 for providing a visual indicator to an X-ray apparatus which may indicate the present position of the radiopaque marker 136 when an X-ray image is taken. In some embodiments, first and second radiopaque markers 136A and 136B may be aligned in series along the longitudinal axis of each respective radially extending arm 112 as shown in FIGS. 2, 9 and 10. In other embodiments, each radiopaque marker 136 may define a single radiopaque marker or a plurality of radiopaque markers 136. In some embodiments, each of the radiopaque markers 136 may define a circular-shaped configuration, a square-shaped configuration, a rectangular-shaped configuration, an oval-shaped configuration, an asymmetrical-shaped configuration, a symmetrical-shaped configuration, and/or an angular-shaped configuration. In some embodiments, one or more radiopaque markers 136 may extend along the longitudinal axis of each respective radially extending arm 112. In some embodiments, the entire rotatable wheel 110 may be made from a radiopaque material or only the radially extending arms 112 may be made from a radiopaque material. In some embodiments, each of the radiopaque markers 136 may have the same configuration or different configurations. In some embodiments, the radiopaque markers 136 may each have a respective numerical designation.

Referring to FIGS. 1, 9 and 10, in some embodiments an elongated channel 106 defines a lumen that establishes a fluid pathway between the inlet port 116 and the outlet port 118 of the casing 102. In some embodiments, the channel 106 defines a distal portion 138 in communication with the outlet port 118, a central portion 139 in communication with the wheel housing 108, and a proximal portion 140 in communication with the inlet port 116. As shown, the distal portion 138 of the channel 106 communicates with the inlet port 116 through a proximal opening 144 and the proximal portion 140 communicates with the outlet port 118 through a distal opening 142. As further shown, a central portion 139 of the channel 106 communicates with a lateral opening 120 of the wheel housing 108 such that at least one of the radially extending arms 112 of the rotatable wheel 110 extends into the channel 106. This structural arrangement between the rotatable wheel 110 and the channel 106 allows the fluid flow detector 100 to detect the presence of cerebrospinal fluid any time the rotatable wheel 110 is made to rotate due to the force applied by the flow of cerebrospinal fluid against one or more of the radially extending arms 112.

In some embodiments, one or more radiopaque reference markers 134 along the casing 102 provide a fixed visual reference for determining whether any movement of a radiopaque marker 136 has occurred over time when fluid flow through the fluid flow detector 100 occurs. The radiopaque reference markers 134 may be made from a radiopaque material positioned at particular locations along the casing 102 as shown in FIG. 10. In some embodiments, the fluid flow detector 100 includes three sets of radiopaque reference markers 134A, 134B and 134C. As shown, radiopaque reference marker 134A may be a single radiopaque marker 134 positioned proximate the central portion 139 of channel 106, radiopaque reference markers 134B may be a pair of radiopaque markers positioned between the outlet port 118 and the wheel housing 108, and radiopaque reference markers 134C may be three aligned radiopaque markers positioned between the inlet port 116 and the wheel housing 108. In other embodiments, any number of radiopaque reference markers 134 may be positioned along the casing 102 to provide a fixed visual reference for determining whether the radiopaque marker(s) 136 on the rotatable wheel 110 have moved when cerebrospinal fluid flows through the channel 106. In some embodiments, only one radiopaque reference marker 134 may be used as a visual reference.

As noted above, the flow of cerebrospinal fluid through the channel 106 applies a force to one or more of the radially extending arms 112 of the rotatable wheel 110 that extend into the channel 106 through the lateral opening 120 of the wheel housing 108 as illustrated in FIG. 10. As such, rotary movement B of the radially extending arms 112 changes the position of the radiopaque markers 136 relative to the fixed radiopaque reference markers 134, thereby providing a visual indication of flow A of cerebrospinal fluid through the fluid flow detector 100.

Figure 12:
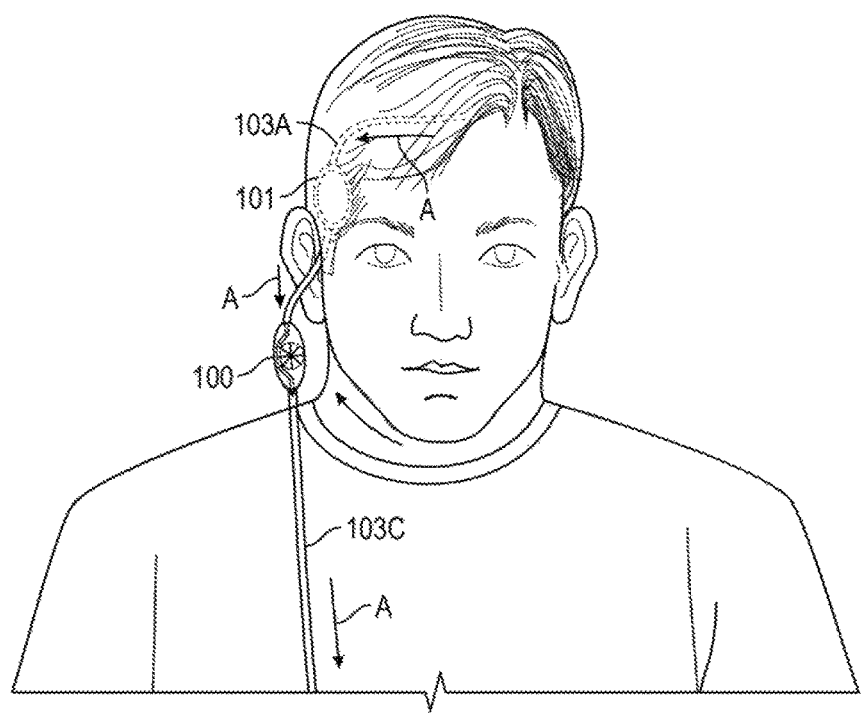
FIG. 12 is an enlarged view of the simplified illustration of FIG. 11, according to one aspect of the present disclosure.

Referring to FIGS. 11 and 12, in some embodiments the fluid flow detector 100 may communicate with a catheter 103B which is coupled between the inlet port 116 of the casing 102 and a shunt reservoir and valve component 101. The shunt reservoir and valve component 101 stores excess cerebrospinal fluid that flows through a ventricular catheter 103A disposed within the ventricle of an individual. As further shown, one end of a catheter 103C is coupled to the outlet port 118 of the fluid flow detector 100 and the opposite end of the catheter 103C terminates within a peritoneal cavity of the individual. In this arrangement, fluid flow A of cerebrospinal fluid from the ventricle of the individual is stored in the shunt reservoir and valve component 101 which is operable to periodically pass the cerebrospinal fluid through the fluid flow detector 100. Once fluid flow A of cerebrospinal fluid exits the fluid flow detector 100, the cerebrospinal fluid is allowed to flow into the peritoneal cavity of the individual. As further shown, an X-ray apparatus 190 may be implemented to capture X-ray images associated with the radiopaque markers 136 of the fluid flow detector 100. Specifically, as shown in FIG. 11, the X-ray apparatus 190 may be oriented over the fluid flow detector 100 to capture X-ray images of the fluid flow detector 100, which may reveal a movement of the radiopaque markers 136, as described herein.

Figure 13:
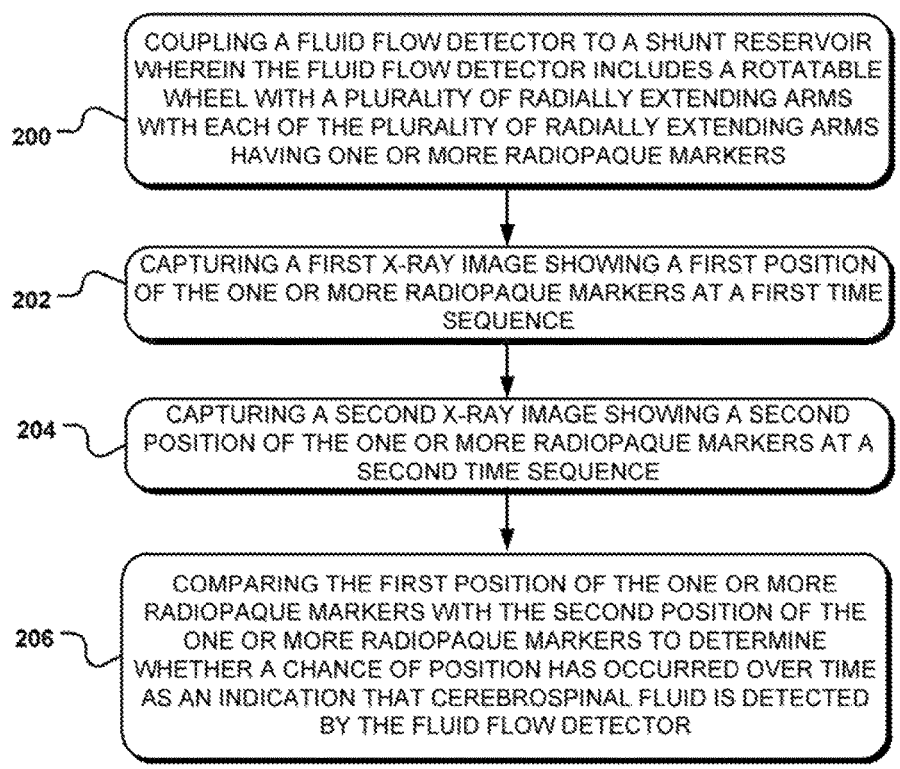
FIG. 13 is a flow chart illustrating one method for detecting fluid flow using the fluid flow detector to detect the presence of cerebrospinal fluid, according one aspect of the present disclosure.

One method of detecting cerebrospinal fluid is illustrated in the flow chart shown in FIG. 13. Block 200 of FIG. 13 involves coupling a fluid flow detector to a flow source such as a shunt reservoir. The fluid flow detector includes a rotatable wheel with a plurality of radially extending arms with each of the plurality of radially extending arms having one or more radiopaque markers. At block 202, a first X-ray image is captured showing a first position of one or more radiopaque markers at a first time sequence. At block 204, a second X-ray image is captured showing a second position of the one or more radiopaque markers at a second time sequence. At block 206 comparing the first position of the one or more radiopaque markers with the second position of the one or more radiopaque markers to determine whether a change of position of the one or more radiopaque markers has occurred over time which provides a visual indication of cerebrospinal fluid flow through the fluid flow detector.

In some embodiments, the method of FIG. 13 may further include determining a time value associated with a change in time between the first time sequence and the second time sequence; and determining a rate of the fluid flow through the fluid flow detector using the time value associated with the change in time and a position value associated with any difference in position of the radiopaque marker between the first time sequence and the second time sequence.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A fluid flow detector, comprising:
a casing defining an interior chamber;
a rotatable wheel disposed within interior chamber of the casing, the rotatable wheel including an axle and a plurality of radially extending arms extending from the axle, wherein at least one of the plurality of radially extending arms includes a radiopaque marker; and
a fluid pathway extending through the casing, wherein the fluid pathway is in fluid flow communication with at least one of the radially extending arms of the rotatable wheel;
wherein the rotatable wheel rotates about an axis defined by the axle and arranged within the interior chamber such that the flow of fluid through the fluid pathway causes movement of the plurality of radially extending arms and provides a visual indication of fluid flow through the channel based on a difference in position of the radiopaque marker when the rotatable wheel is rotated by the flow of fluid through the fluid pathway.

2. The fluid flow detector of claim 1, further comprising a wheel housing defining a lateral opening in fluid flow communication with the pathway which defines a channel that forms, wherein at least one of the plurality of radially extending arms extends through the lateral opening of the wheel housing and into the lumen of the channel such that the flow of the fluid through the channel applies a force to at least one of the plurality of radially extending arms to cause rotation of the rotatable wheel.

3. The fluid flow detector of claim 2, further comprising:
an inlet port in fluid flow communication with one end of the fluid pathway and an outlet port in fluid flow communication with an opposite end of the fluid pathway, wherein the inlet port is in fluid flow communication with a source of fluid.

4. The fluid flow detector of claim 1, wherein a position of the radiopaque marker is detectable through the casing via an X-ray apparatus.

5. The fluid flow detector of claim 1, further comprising:
at least one reference radiopaque marker on the casing for providing a visual reference with respect to the radiopaque marker on the radially extending arm, the at least one reference radiopaque marker being detectable by the X-ray apparatus.

6. The fluid flow detector of claim 5, wherein the radiopaque marker and the at least one reference radiopaque marker defines a circular-shaped configuration, a square-shaped configuration, a rectangular-shaped configuration, an angular configuration, a symmetrical configuration, an asymmetrical configuration, and/or oval configuration.

7. The fluid flow detector of claim 1, wherein the radiopaque marker defines a numerical designation.

8. The fluid flow detector of claim 2, wherein the wheel housing defines a lateral opening in fluid flow communication with the fluid pathway.

9. The fluid flow detector of claim 8, wherein the fluid pathway is formed through a channel defining a lumen and wherein the lateral opening is in fluid flow communication with the lumen of the channel such that at least one of the plurality of radially extending arms extends into the channel from the wheel housing.

10. A fluid flow detector system, comprising:
a fluid flow detector, comprising
a casing defining an interior chamber and a channel formed through the casing and disposed within the interior chamber for establishing fluid flow communication between an inlet port and an outlet port;
a rotatable wheel disposed within the interior chamber, the rotatable wheel defining an axle with a plurality of arms extending radially from the axle; and
a radiopaque marker associated with at least one of the plurality of arms; and
wherein rotation of the rotatable wheel when fluid flows through the channel causes movement of the radiopaque marker as the plurality of arms rotates and provides a visual indication of fluid flow through the fluid flow detector.

11. The fluid flow detector system of claim 10, further comprising:
a shunt reservoir and valve component in fluid flow communication with the channel of the fluid flow detector for passing fluid into the channel of the fluid flow detector.

12. The fluid flow detector system of claim 10, further comprising:

an X-ray apparatus for taking a first X-ray image of the casing at a first time sequence and a second X-ray image of the casing at a second time sequence.

13. The fluid flow detector system of claim 10, further comprising:
a reference radiopaque marker on the casing for providing a visual reference relative to the radiopaque marker on the radially extending arm.

14. The fluid flow detector system of claim 12, wherein the X-Ray apparatus is utilized to compare the first X-ray image of the radiopaque marker with the second X-ray image of the radiopaque marker to determine whether movement of the radiopaque marker has occurred.

15. A method, comprising:
coupling a fluid flow detector to a source of fluid, the fluid flow detector comprising a casing defining an interior chamber, a rotatable wheel defining a plurality of radially extending arms disposed within the interior chamber of the casing, and a fluid pathway extending through the casing and in fluid flow communication with the rotatable wheel, wherein the rotatable wheel includes a radiopaque marker, and wherein the flow of fluid through the fluid pathway applies a force to the radially extending arms causing the rotatable wheel to rotate and change the position of the radiopaque marker;
capturing a first x-ray image at a first position of the radiopaque marker at a first time sequence;
capturing a second x-ray image showing a second position of the radiopaque marker at a second time sequence; and
comparing the first position of the radiopaque marker with the second position of the radiopaque marker to identify a change in position of the radiopaque marker indicative of a fluid flow through the fluid flow detector.

16. The method of claim 15, further comprising:
providing a reference radiopaque marker on the casing for establishing a fixed visual reference relative to the radiopaque marker on the plurality of arms.

17. The method of claim 15, further comprising:
determining a time value associated with a change in time between the first time sequence and the second time sequence; and
determining a rate of the fluid flow through the fluid flow detector using the time value associated with the change in time and a position value associated with any difference in position of the radiopaque marker between the first time sequence and the second time sequence.

18. The method of claim 15, further comprising:
coupling a first end of a catheter to the fluid pathway of the fluid flow detector and disposing a second end of the catheter within the peritoneal cavity of an individual.

* * * * *